(12) United States Patent
Mills

(10) Patent No.: US 10,298,887 B2
(45) Date of Patent: May 21, 2019

(54) MULTI-CHROMATIC IMAGING SYSTEM AND METHOD

(75) Inventor: Stewart Mills, London (GB)

(73) Assignee: BUHLER SORTEX LTD, London (GB)

( * ) Notice: Subject to any disclaimer, the term of this patent is extended or adjusted under 35 U.S.C. 154(b) by 670 days.

(21) Appl. No.: 13/510,572

(22) PCT Filed: Nov. 17, 2010

(86) PCT No.: PCT/GB2010/002118
§ 371 (c)(1),
(2), (4) Date: Aug. 6, 2012

(87) PCT Pub. No.: WO2011/061490
PCT Pub. Date: May 26, 2011

(65) Prior Publication Data
US 2013/0113918 A1    May 9, 2013

(30) Foreign Application Priority Data
Nov. 17, 2009   (GB) .................................. 0920177.3

(51) Int. Cl.
*H04N 7/18*   (2006.01)
*H04N 9/47*   (2006.01)
(Continued)

(52) U.S. Cl.
CPC ............... *H04N 9/04* (2013.01); *G01N 21/31* (2013.01); *G01N 21/85* (2013.01)

(58) Field of Classification Search
CPC .......... H04N 9/04; G01N 21/31; G01N 21/85; G01N 21/8806; G01N 21/8903; B07C 5/342
(Continued)

(56) References Cited

U.S. PATENT DOCUMENTS 6,078,018 A    6/2000   Davis et al.
2003/0098978 A1    5/2003   Ikeda et al.
(Continued)

FOREIGN PATENT DOCUMENTS

WO    09/137854 A1    11/2009

OTHER PUBLICATIONS

International Search Report for Application No. PCT/GB2010/002118, 5 pages, dated Apr. 19, 2011.

*Primary Examiner* — Jessica M Prince
(74) *Attorney, Agent, or Firm* — Nelson Mullins Riley & Scarborough LLP; Anthony A. Laurentano

(57) ABSTRACT

An imaging system for and method of imaging product in a product flow (F), the system comprising: an illumination unit for illuminating product in the product flow with illumination at first and second, different wavelengths or ranges of different wavelengths; a detector unit (15) for detecting reflected illumination from product in the product flow, wherein the detector unit comprises first and second line array detectors, the line array detectors (17a, 17b) each comprising a plurality of pixel elements and extending as lines across a width of the product flow, one line downstream of the other, whereby product passing a pixel element of the first line array detector passes a corresponding pixel element of the second line array detector; a control unit for triggering the first and second illumination sources to flash sequentially at a scan rate corresponding to the flow rate of the product flow; and an image processing unit for successively reading the pixel lines of the first and second line array detectors and constructing images of the product at each of the illumination wavelengths or ranges of illumination wavelengths.

16 Claims, 5 Drawing Sheets

(51) Int. Cl.
*H04N 9/04* (2006.01)
*G01N 21/31* (2006.01)
*G01N 21/85* (2006.01)

(58) Field of Classification Search
USPC .......................................................... 348/91
See application file for complete search history.

(56) References Cited

U.S. PATENT DOCUMENTS

| | | |
|---|---|---|
| 2004/0052402 A1 | 3/2004 | Hamid |
| 2009/0050540 A1* | 2/2009 | Imai ..................... B07C 5/3425 |
| | | 209/580 |
| 2009/0079970 A1* | 3/2009 | Cohn .................... B07C 5/3427 |
| | | 356/237.1 |
| 2011/0050968 A1 | 3/2011 | Fruehwirth et al. |

* cited by examiner

Scan Period 1

Scan Period 2

Scan Period 3

Scan Period 4

MULTI-CHROMATIC IMAGING SYSTEM AND METHOD

RELATED APPLICATIONS

This application is a 35 U.S.C. 371 national stage filing of International Application No. PCT/GB2010/002118, filed Nov. 17, 2010, which claims priority to Great Britain Patent Application No. 0920177.3 filed on Nov. 17, 2009 in Great Britain. The contents of the aforementioned applications are hereby incorporated by reference.

The present invention relates to a multi-chromatic imaging system and method for multi-chromatic imaging of product in a product flow, in particular in bulk sorting, such as in flows of foodstuff and plastic components, for example, plastic pellets.

Multi-chromatic imaging provides for improved detection of product as compared to mono-chromatic imaging, in providing for characterisation of product based on more than one characteristic. Also, multi-chromatic imaging which utilizes ratios of the intensity of chromatic reflection is advantageous as compared to mono-chromatic imaging which utilizes a single measured intensity, in being less affected by the angle of incidence, especially with respect to edges.

Imaging systems exist for multi-chromatic imaging of product in product flows. One such imaging system is disclosed in US-A-2009/0079970, which provides for the detection of multiple wavelengths using a single photodetector.

It is an aim of the present invention to provide a multi-chromatic imaging system and method for multi-chromatic imaging of product using multiple line array detectors, preferably of lower cost.

In one aspect the present invention provides an imaging system for imaging product in a product flow, the system comprising: an illumination unit for illuminating product in the product flow with illumination at first and second, different wavelengths or ranges of different wavelengths; a detector unit for detecting reflected illumination from product in the product flow, wherein the detector unit comprises first and second line array detectors, the line array detectors each comprising a plurality of pixel elements and extending as lines across a width of the product flow, one line downstream of the other, whereby product passing a pixel element of the first line array detector passes a corresponding pixel element of the second line array detector; a control unit for triggering the first and second illumination sources to flash sequentially at a scan rate corresponding to the flow rate of the product flow; and an image processing unit for successively reading the pixel lines of the first and second line array detectors and constructing images of the product at each of the illumination wavelengths or ranges of illumination wavelengths.

In another aspect the present invention provides an imaging system for imaging product in a product flow, the system comprising: an illumination unit for illuminating product in the product flow with illumination at first and second, different wavelengths or ranges of different wavelengths; a detector unit for detecting reflected illumination from product in the product flow, wherein the detector unit comprises first and second line array detectors, the line array detectors each comprising a plurality of pixel elements and extending as lines across a width of the product flow, one line downstream of the other, whereby product passing a pixel element of the first line array detector passes a corresponding pixel element of the second line array detector; a control unit for triggering the first and second illumination sources to flash sequentially at a scan rate corresponding to the flow rate of the product flow; and an image processing unit for successively reading the pixel lines of the first and second line array detectors to provide for characterization of the product at each of the illumination wavelengths or ranges of illumination wavelengths.

In a further aspect the present invention provides a method of imaging product in a product flow, the method comprising the steps of: illuminating product in the product flow sequentially with illumination at first and second, different wavelengths or ranges of different wavelengths at a scan rate corresponding to the flow rate of the product flow; detecting reflected illumination from product in the product flow, wherein the reflected illumination is detected by first and second line array detectors, the line array detectors each comprising a plurality of pixel elements and extending as lines across a width of the product flow, one line downstream of the other, whereby product passing a pixel element of the first line array detector passes a corresponding pixel element of the second line array detector; and successively reading the pixel lines of the first and second line array detectors and constructing images of the product at each of the illumination wavelengths or ranges of illumination wavelengths.

In a yet further aspect the present invention provides a method of imaging product in a product flow, the method comprising the steps of: illuminating product in the product flow sequentially with illumination at first and second, different wavelengths or ranges of different wavelengths at a scan rate corresponding to the flow rate of the product flow; detecting reflected illumination from product in the product flow, wherein the reflected illumination is detected by first and second line array detectors, the line array detectors each comprising a plurality of pixel elements and extending as lines across a width of the product flow, one line downstream of the other, whereby product passing a pixel element of the first line array detector passes a corresponding pixel element of the second line array detector; and successively reading the pixel lines of the first and second line array detectors to provide for characterization of the product at each of the illumination wavelengths or ranges of illumination wavelengths.

In a preferred embodiment multiple unfiltered line array detectors are utilized which receive reflected radiation through a single lens.

Preferred embodiments of the present invention will now be described hereinbelow by way of example only with reference to the accompanying drawings, in which:

FIG. 1 schematically represents a bi-chromatic imaging system in accordance with a first embodiment of the present invention;

Figure 1:
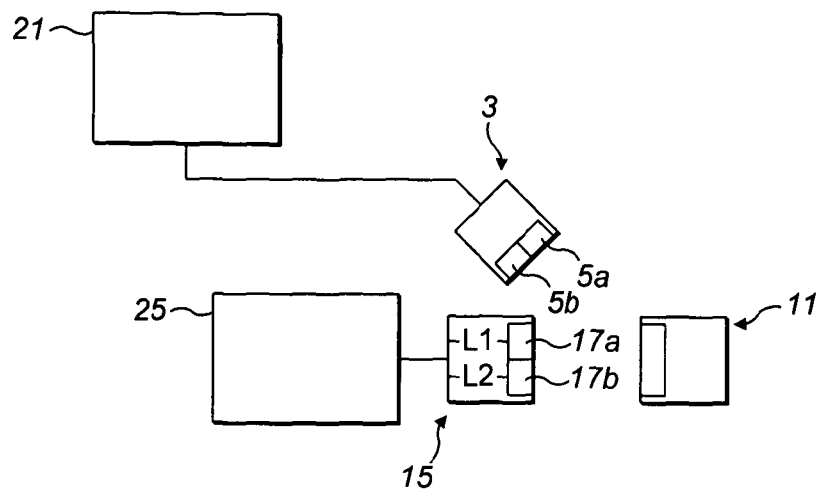
Figure 2A:
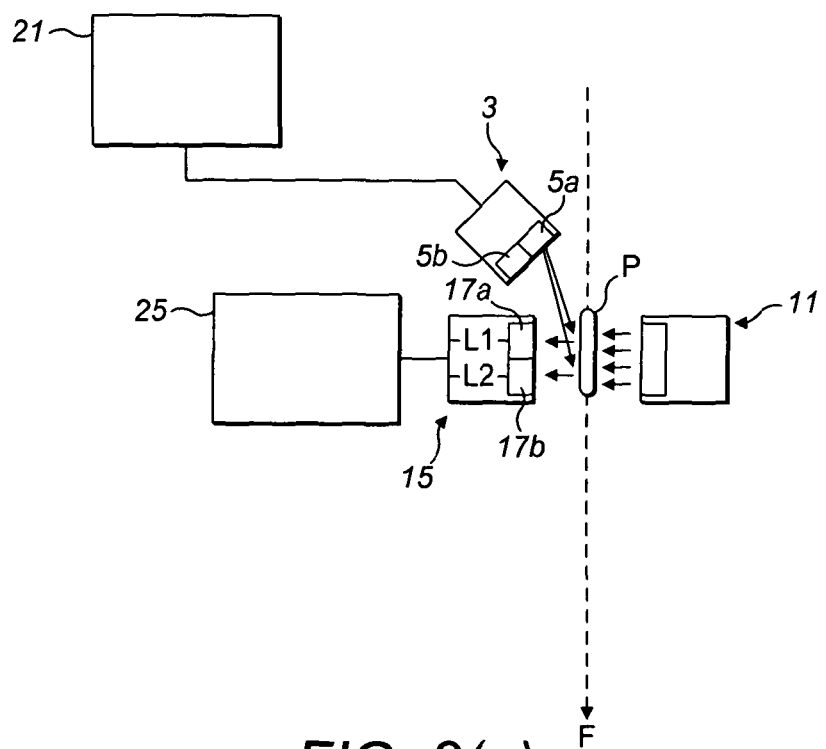
FIG. 2(a) illustrates the imaging system of FIG. 1 in a first imaging phase, in which the product is illuminated with illumination at a first wavelength.
Figure 2B:
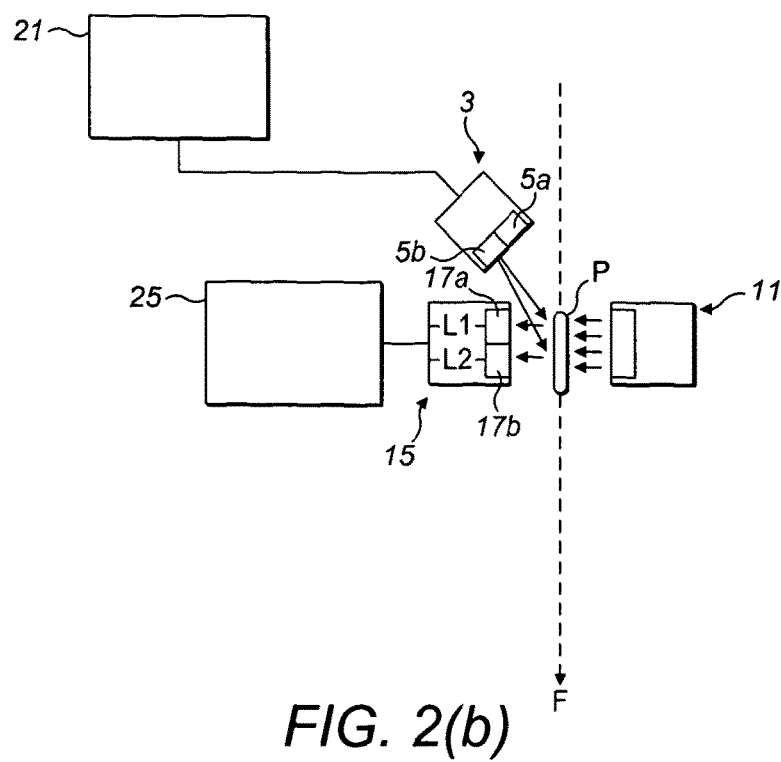
FIG. 2(b) illustrates the imaging system of FIG. 1 in a second imaging phase, in which the product is illuminated with illumination at a second, different wavelength.
Figure 3:
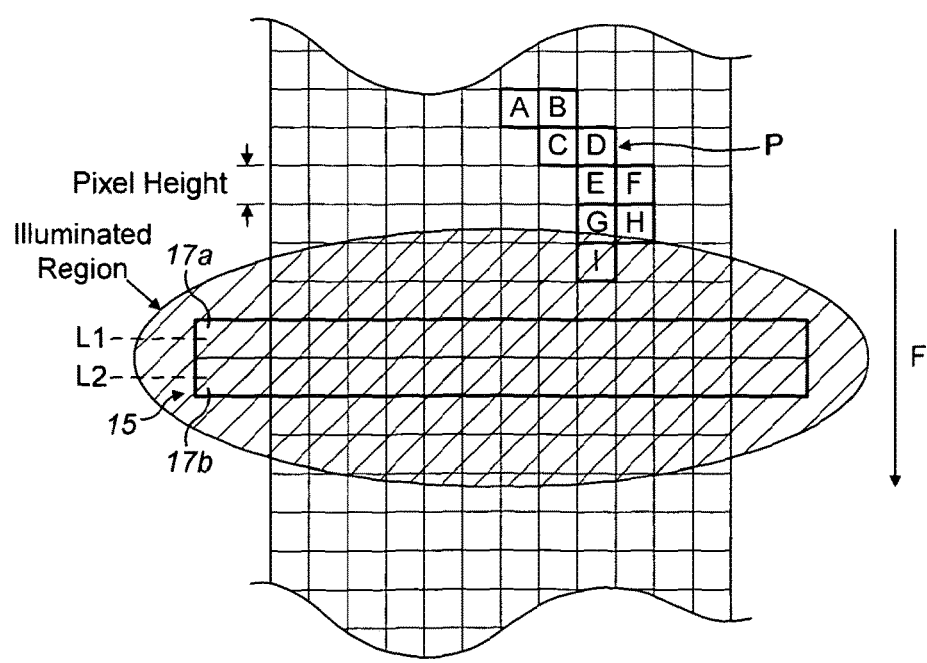
Figure 4A:
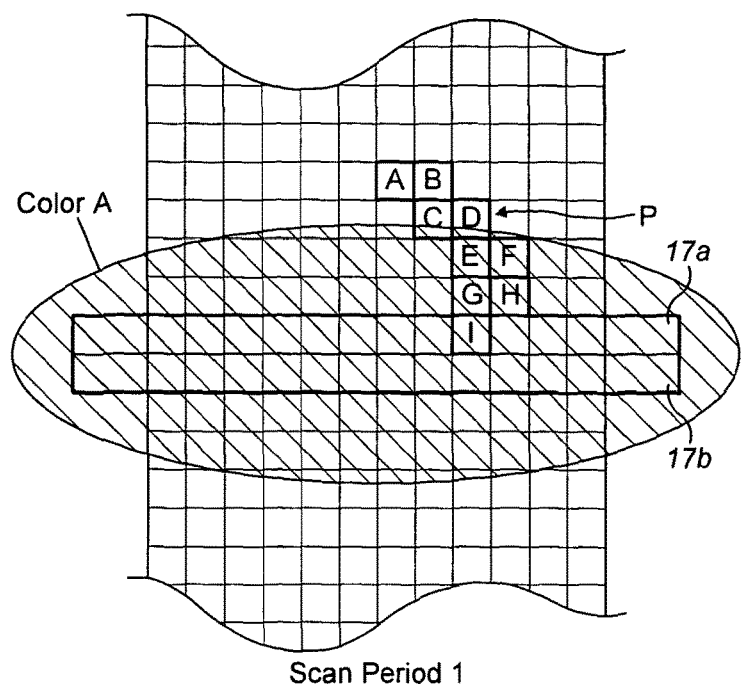
Figure 4B:
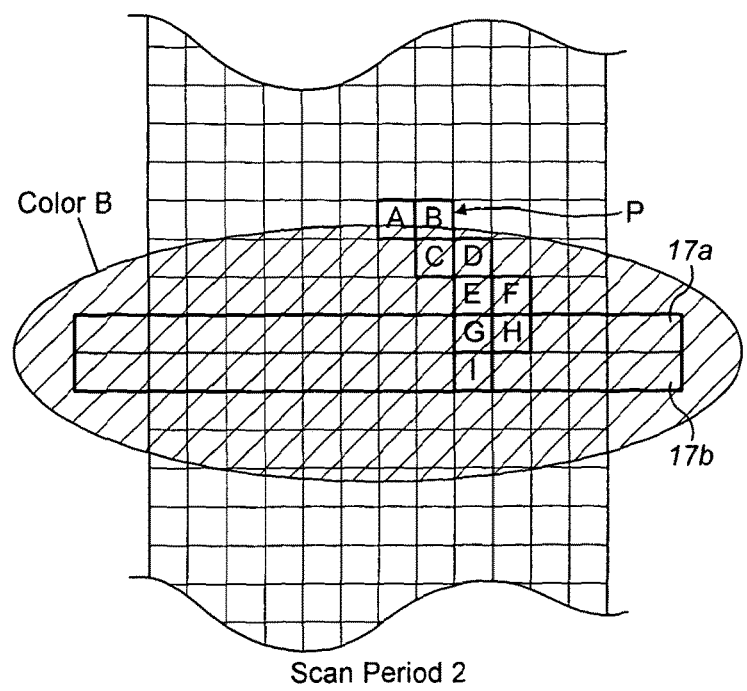
Figure 4C:
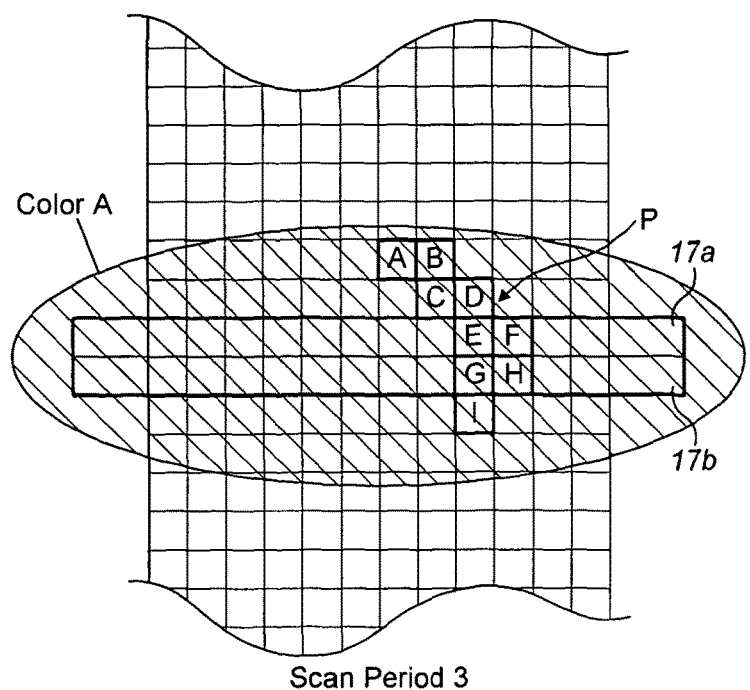
Figure 4D:
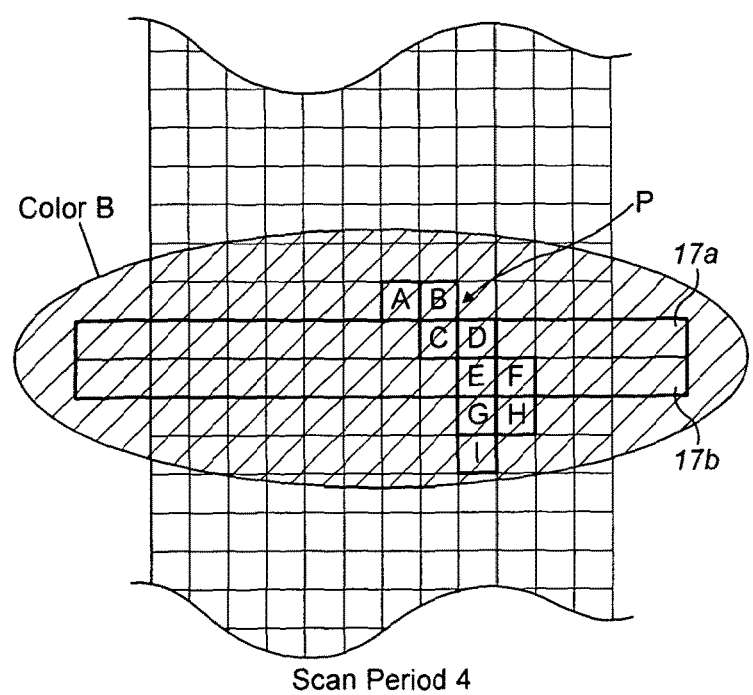
Figure 5:
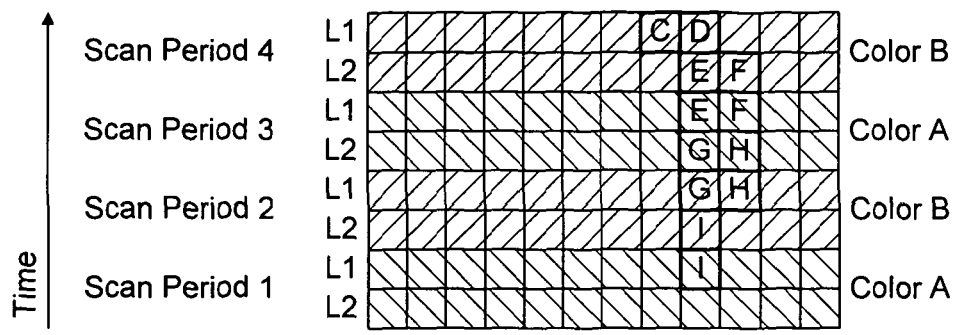
Figure 6:
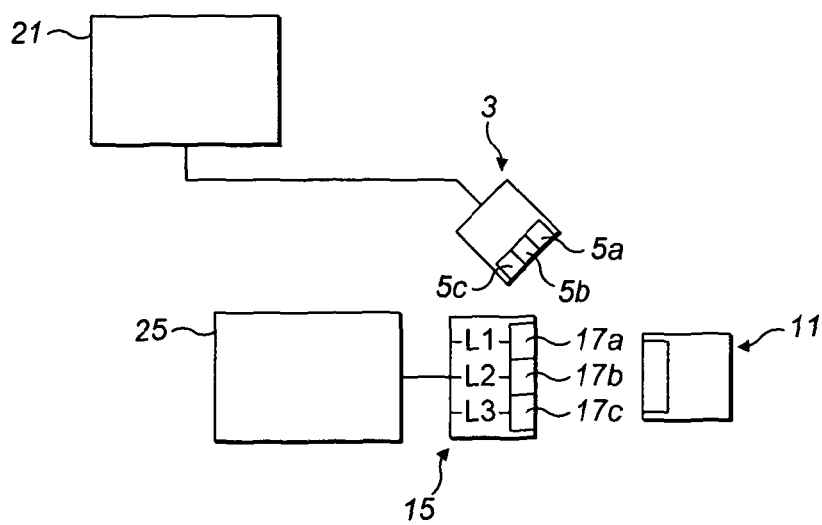

FIG. 3 schematically illustrates a product passing the first and second line array detectors of the imaging system of FIG. 1 in a product flow;

FIGS. 4 (a) to (d) illustrate successive scan periods (scan periods 1-4) as a product passes the first and second line array detectors of the imaging system of FIG. 1 in a product flow;

FIG. 5 schematically represents the accumulated sequence of images for the scan periods (scan periods 1-4) of FIGS. 4(a) to (d); and FIG. 6 schematically represents a tri-chromatic imaging system in accordance with a second embodiment of the present invention.

The imaging system comprises a first, foreground illumination unit 3, in this embodiment an elongate unit, for illuminating product P in a product flow F with illumination at first and second, different wavelengths or ranges of different wavelengths.

In this embodiment the foreground illumination unit 3 comprises first and second illumination sources 5a, 5b, here elongate illumination sources, for respectively providing illumination at first and second, different wavelengths or ranges of different wavelengths. As will be described in more detail hereinbelow, the first and second illumination sources 5a, 5b are triggered sequentially to flash at a scan rate.

In this embodiment the illumination sources 5a, 5b comprise semiconductor illumination sources, here LEDs arranged in rows.

The first and second wavelengths could, for example, be those of different colors, for example, red and green light, with the wavelengths or spectrums of wavelengths being determined by characteristics of the product P to be detected.

The imaging system further comprises a second, background illumination unit 11 for illuminating the product flow F with a reference, background illumination.

In this embodiment the background illumination unit 11 provides background illumination at a fixed wavelength or range of wavelengths.

In an alternative embodiment the background illumination unit 11 could comprise first and second background illumination sources to provide background illumination at first and second, different wavelengths or ranges of different wavelengths, with the first and second background illumination sources being triggered sequentially to flash at the scan rate. With this configuration, the background illumination can be moved in the intensity space in relation to the foreground, detection illumination, which, in some circumstances, could provide for improved detection.

The imaging system further comprises a detector unit 15 for detecting reflected illumination from product P in the product flow F, in this embodiment comprising first and second line array detectors 17a, 17b.

In this embodiment the line array detectors 17a, 17b each comprise a plurality of pixel elements and extend across the width of the product flow F.

The first and second line array detectors 17a, 17b are located one downstream of the other and are arranged as lines L1, L2 which extend across the product flow F, whereby product P passing a pixel element of the first line array detector 17a passes a corresponding pixel element of the second line array detector 17b.

In this embodiment the first and second line array detectors 17a, 17b are juxtaposed.

In an alternative embodiment the first and second line array detectors 17a, 17b could be spaced.

In this embodiment the first and second line array detectors 17a, 17b comprise linear CCD array detectors, which provide for UV, visible light and infrared (IR) detection.

In this embodiment the first and second line array detectors 17a, 17b are unfiltered line array detectors which receive reflected radiation through a single, common lens.

In an alternative embodiment one or both of the first and second line array detectors 17a, 17b could comprise InGaAs array detectors, which would provide for infrared (IR) and longer wavelength detection.

The imaging system further comprises a control unit 21 for triggering the first and second illumination sources 5a, 5b to flash sequentially at a scan rate corresponding to the flow rate of the product flow F, that is, at a time interval in which product P passes from the centre of the first line array detector 17a to the centre of the second line array detector 17b, whereby the first illumination source 5a is flashed when the product P is located adjacent the first line array detector 17a and the second illumination source 5b is flashed when the product P is located adjacent the second line array detector 17b.

In this embodiment the control unit 21 is operative to determine the flow rate of the product flow F by detecting the time period for product P to pass from the first line array detector 17a to the second line array detector 17b, and set the scan rate accordingly. By actively detecting the flow rate of the product flow F, improved registration of the product P to the first and second line array detectors 17a, 17b in relation to the flashing of the illumination sources 5a, 5b can be achieved.

In an alternative embodiment a separate speed sensor could be employed to determine the flow rate of the product flow F, with the scan rate being set accordingly.

In another embodiment the scan rate could be pre-set based on a prior determination of the flow rate of the product flow F.

The imaging system further comprises an image processing unit 25 for successively reading the pixel lines of the first and second line array detectors 17a, 17b and provide complete images for each of the illumination wavelengths.

FIG. 3 schematically illustrates a product P, here irregularly shaped, which is represented in terms of pixel elements A-I, passing the first and second line array detectors 17a, 17b in the product flow F.

FIGS. 4(a) to (d) illustrate successive scan periods (scan periods 1-4) as the product P passes the first and second line array detectors 17a, 17b in the product flow F, with the illumination of the successive scans being switched between the first and second wavelengths or range of wavelengths, here exemplified as colors A and B.

FIG. 5 schematically represents the accumulated sequence of images for the scan periods (scan periods 1-4) of FIGS. 4(a) to (d).

In this embodiment, for each illumination wavelength or range of wavelengths, the pixel lines L1, L2 of the first and second line array detectors 17a, 17b are combined to provide a single complete wavelength image, with the image for the first wavelength illumination comprising the repeat L1, L2, L1, . . . and the image for the second wavelength illumination comprising the repeat L2, L1, L2, . . . .

Finally, it will be understood that the present invention has been described in its preferred embodiments and can be modified in many different ways without departing from the scope of the invention as defined by the appended claims.

For example, in one alternative embodiment the foreground illumination unit 3 could comprise a single illumination source 5, here an elongate illumination source, which selectively provides illumination at first and second, different wavelengths. In this embodiment the illumination source 5 could comprise a semiconductor illumination source, here multi-wavelength LEDs arranged in rows.

In another modification, as illustrated in FIG. 6, the imaging system could provide for tri-chromatic imaging or n-chromatic imaging, where n is greater than 3. In this tri-chromatic embodiment the illumination unit 3 comprises three illumination sources 5a, 5b, 5c for providing illumination at three different wavelengths or ranges of wavelengths, and the detector unit 15 comprises three line array detectors 17a, 17b, 17c arranged as three adjacent lines L1, L2, L3 across the width of the product flow F. In this embodiment, for each illumination wavelength or ranges of wavelengths, the pixel lines L1, L2, L3 of the first, second and third line array detectors 17a, 17b, 17c are combined to provide a single complete wavelength image, with the image for the first wavelength illumination comprising the repeat L1, L2, L3, L1, . . . , the image for the second wavelength illumination comprising the repeat L2, L1, L2, L3, . . . and the image for the third wavelength illumination comprising the repeat L3, L1, L2, L3, . . . .

The invention claimed is:

1. An imaging system for imaging a product in a product flow, the system comprising:
  an elongate illuminator for illuminating the product in the product flow with visible light, infrared (IR) and/or UV illumination at first and second, different wavelengths or ranges of different wavelengths;
  a detector for detecting reflected illumination from the product in the product flow, wherein the detector comprises first and second line array detectors, each of the first and second line array detectors comprising a plurality of pixel elements arranged as a pixel line which extends across the product flow, wherein the pixel line of the second line array detector is located downstream of the pixel line of the first line array detector, whereby product detected by a pixel element of the pixel line of the first line array detector is subsequently detected by a corresponding pixel element of the pixel line of the second line array detector;
  a controller for triggering the elongate illuminator to flash at a scan rate corresponding to the flow rate of the product flow; and
  an image processor for reading the pixel lines of the first and second line array detectors at successive scan periods and constructing wavelength images of the product at each of the first and second different wavelengths or ranges of different wavelengths and combining accumulated pixel line readings from successive scan periods, in order to characterize the product based on a ratio of intensity of chromatic reflection for the first and second different wavelengths or ranges of different wavelengths.

2. The imaging system of claim 1, wherein the illuminator comprises first and second illumination sources which each comprise
  light emitting diodes (LEDs) arranged in a row.

3. The imaging system of claim 1, further comprising:
  a further illuminator for illuminating the product flow with a reference, background illumination.

4. The imaging system of claim 3, wherein the further illuminator comprises first and second illumination sources for providing background illumination at first and second, different wavelengths or ranges of different wavelengths, with the first and second background illumination sources being triggered by the controller sequentially to flash at the scan rate.

5. The imaging system of claim 1, wherein the first and second line array detectors receive reflected radiation through a single, common lens.

6. The imaging system of claim 1, wherein at least one of the first and second line array detectors comprises a linear charge coupled device (CCD) array detector and/or an indium gallium arsenide (InGaAs) array detector.

7. The imaging system of claim 1, wherein the controller is operative to determine the flow rate of the product flow either by detecting the time period for product to pass between the pixel line of the first line array detector and the pixel line of the second line array detector or by means of a separate speed sensor.

8. The imaging system of claim 1, wherein the detector comprises a third line array detector comprising a plurality of pixel elements arranged as a third pixel line which extends across the product flow, and the image processor reads the pixel lines of the first, second and third line array detectors at successive scan periods and constructs wavelength images of the product at each of the first and second different wavelengths or ranges of different wavelengths.

9. A method of imaging a product in a product flow, the method comprising the steps of:
  illuminating product in the product flow with visible light, infrared (IR) and/or UV illumination at first and second, different wavelengths or ranges of different wavelengths;
  detecting reflected illumination from product in the product flow, wherein the reflected illumination is detected by first and second line array detectors, each of the first and second line array detectors comprising a plurality of pixel elements arranged as a pixel line which extends across the product flow, wherein the pixel line of the second line array detector is located downstream of the pixel line of the first line array detector, whereby product detected by a pixel element of the pixel line of the first line array detector is subsequently detected by a corresponding pixel element of the pixel line of the second line array detector; and
  reading the pixel lines of the first and second line array detectors at successive scan periods at a scan rate corresponding to a flow rate of the product and constructing wavelength images of the product at each of the first and second different wavelengths or ranges of different wavelengths by combining accumulated pixel line readings from successive scan periods, in order to characterize the product based on a ratio of intensity of chromatic reflection for the first and second different wavelengths or ranges of different wavelengths.

10. The method of claim 9, wherein the illumination at first and second different wavelengths or ranges of different wavelengths is provided by first and second illumination sources which each comprise light emitting diodes (LEDs) arranged in a row.

11. The method of claim 9, further comprising the step of:
  illuminating the product flow with a further, reference, background illumination.

12. The method of claim 11, wherein the background illumination is provided at first and second, different wavelengths or ranges of different wavelengths flashed sequentially at the scan rate.

13. The method of claim 9, wherein the first and second line array detectors receive reflected radiation through a single, common lens.

14. The method of claim 9, wherein at least one of the first and second line array detectors comprises a linear charge coupled device (CCD) array detector and/or an indium gallium arsenide (InGaAs) array detector.

15. The method claim 9, further comprising the step of:
  (I) determining the flow rate of the product flow by detecting the time period for product to pass between the pixel line of the first line array detector and the pixel line of the second line array detector; or (II) determining the flow rate of the product flow using a speed sensor.

16. The method of claim 9, wherein the step of detecting reflected illumination further comprises the step of:

detecting reflected illumination from product in the product flow by a third line array detector comprising a plurality of pixel elements arranged as a pixel line which extends across the product flow and reading the pixel lines of the first, second and third line array detectors at successive scan periods to construct wavelength images of the product at each of the first and second different wavelengths or ranges of different wavelengths.

* * * * *